United States Patent [19]
Djordjevic

[11] Patent Number: 6,020,146
[45] Date of Patent: Feb. 1, 2000

[54] CARCINOGENICITY TESTING SYSTEM

[75] Inventor: Bozidar Djordjevic, Astoria, N.Y.

[73] Assignee: The Research Foundation State University of New York, Albany, N.Y.

[21] Appl. No.: 08/932,327

[22] Filed: Sep. 17, 1997

Related U.S. Application Data

[60] Provisional application No. 60/026,310, Sep. 18, 1996.

[51] Int. Cl.$^7$ .................. G01N 33/567; A61K 39/395; C07K 16/44; C12Q 1/24
[52] U.S. Cl. .................. 435/7.23; 435/7.1; 435/29; 435/30; 435/7.21; 435/375; 435/376; 435/383; 435/345; 436/503; 436/94; 530/388.9; 514/49
[58] Field of Search .................. 435/7.1, 29, 30, 435/7.23, 7.21, 375, 376, 383; 436/503, 94; 530/388.9; 514/49

[56] References Cited

U.S. PATENT DOCUMENTS 5,023,172  6/1991  Djordjevic .

OTHER PUBLICATIONS

Selden et al Cytometry vol. 14 154–157, 1993.
Selden et al Mutation Research, DNA Repair vol. 315 147–167, 1994.
Cunningham et al Environmental Health Perspectives vol. 101 Supplement 5 253–258, 1993.
Vanderlaan et al Cytometry vol. 7 499–507, 1986.
Borek (1985) "Oncogenes and Cellular Controls in Radiogenic Transformation of Rodent and Human Cells", *Carcinogenesis 10*:303–316.
Dahle, et al. (Mar. 4, 1997) "Cooperative Effects of Photodynamic Treatment of Cells in Microcolonies", *Proceedings of the National Academy of Sciences of the United States of America 94*(5):1773–1778, Abstract No. 97203136.
Djordjevic, et al. (1990) "Clonogenicity of Mammalian Cells in Hybrid Spheroids: A New Assay Method", *Radiat. Environ. Biophys. 29*:31–46.
Djordjevic, et al. (1993) "Response of Primary Colon Cancer Cells in Hybrid Spheroids to 5–Fluorouracil", *Cancer Investigation 11*(3):291–298.
Girardi, et al. "SV$_{40}$–Induced Transformation of Human Diploid Cells: Crisis and Recovery", *J. Cell. and Comp. Physiol. 65*:69–84, (1965).
Grill, et al. (Mar.–Apr. 1996) "The Presence of Implant Materials Influences Fibronectin Arrangement and Cell Growth in Fibroblast Cultures", *Bollettino—Societa Italiana Biologia Sperimentale 72*(3–4):87–94, Abstract No. 96367794.
Hanawalt (Dec. 23, 1994) "Transcription–Coupled Repair and Human Disease", *Science 266*:1957–1960.
Kallio, et al. (Jul. 1995) "Early G1 in the Male Rat Meiotic Cell Cycle is Hypersensitive to N–Methyl–N–Nitrosourea–Induced Micronucleus Formation", *Mutagenesis 10*(4):279–285, Abstract No. 96003998.
Kim, et al. (Dec. 23, 1994) "Specific Association of Human Telomerase Activity with Immortal Cells and Cancer", *Science 266*:2011–2015.
Kohri, et al. (1990) "Effect of High Energy Shock Waves on Tumor Cells", *Urol. Res. 18*:101–105.
Koshland, Jr. (Dec. 23, 1994) "Molecule of the Year: The DNA Repair Enzyme", *Science 266*:1925–1927.
Kfaeft, et al. (Dec. 1993) "Bromodeoxyuriding Distribution Patterns in L 929 Fibroblasts and Influence of Tumor Necrosis Factor", *European Journal of Cell Biology 62*(2):415–421, Abstract No. 95010170.
Linares–Cruz, et al. (Jan. 1995) "Combined Analysis of in situ Hybridization, Cell Cycle and Structural Markers Using Reflectance and Immunofluorescence Confocal Microscopy", *Histo–chemical Journal 27*(1):15–23, Abstract No. 95229436.
Mossin, et al. (Oct. 1994) "Ploidy–Dependent Growth and Binucleation in Cultured Rat Hepatocytes", *Experimental Cell Research 214*(2):551–560, Abstract No. 95010352.
Moretto, et al. (Mar. 5, 1993) "Human Astrocytes and Cytokines: Tumor Necrosis Factor Alpha and Interferon Gamma do not Promote Astrocytic Proliferation", *Neuroscience Letters 151*(1):17–20, Abstract No. 93226239.
Mukhopadhyay, et al. (Jan. 1995) "Cytokinetic Studies of Oral Cancer Cells Using Bromodeoxyuridine Labelling in Relation to Factors Influencing Prognosis", *European Journal of Cancer, Part B, Oral Oncology 31B*(1):32–36, Abstract No. 95353174.
Murray, et al. (Nov. 3, 1989) "Dominoes and Clocks: The Union of Two Views of the Cell Cycle", *Science 246*:614–621.
Ohno, et al. (1982) "Inducibility of Sister–Chromatid Exchanges by Heavy–Metal Ions", *Mutation Research 104*:141–145.
Pereira (1993) "Comparison in C3H and C3B6F1 Mice of the Sensitivity to Diethylnitrosamine–Initiation and Phenobarbital–Promotion to the Extent of Cell Proliferation", *Carcinogenesis 14*(2):299–302.
Raffetto, et al. (1979) "Relationship Between Cytotoxicity and Induction of Sister–Chromatid Exchanges in Mouse Foetal Cells Exposed to Several Doses of Carcinogenic and Non–Carcinogenic Chemicals", *Mutation Research 63*:335–343.
Rennie, et al,. (Aug. 1994) "Growth–Promoting Interactions Between the Murine Neocortex and Thalamus in Organotypic Co–Cultures", *Neuroscience 61*(3):547–564, Abstract No. 95059959.
Risio, et al. (1994) "Mucosal Cell Proliferation in Patients with Hyperplastic Colorectal Polyps", *Mucosal Proliferation and Hyperplastic Polyps*:344–348.
Russo, et al. (Mar. 1994) "Evaluation of Sister–Chromatid Exchanges in Mouse Spermatogonia: A comparison Between the Classical Fluorescence Plus Giemsa Staining and an Immunocytochemical Approach", *Mutation Research 323*(3):143–149, Abstract No. 94150497.

(List continued on next page.)

*Primary Examiner*—Julie Reeves
*Attorney, Agent, or Firm*—Scully, Scott, Murphy & Presser

[57] ABSTRACT

The present invention is directed to an in vitro method for detecting the presence of carcinogenic agents.

1 Claim, No Drawings

OTHER PUBLICATIONS

Sakiyama, et al. (Sep. 1978) "Effects of Confluent Monolayers of Density–Inhibited and –Transformed Cells on the Growth of Superinoculated Cells", *Cancer Research 38*:2854–2858.

Sancar (Dec. 23, 1994) "Mechanisms of DNA Excision Repair", *Science 266*:1954–1960.

Speel, et al. (Jul. 1994) "Combined Immunocytochemistry and fluorescence in situ Hybridization for Simultaneous Tricolor Detection of Cell Cycle, Genomic, and Phenotypic Parameters of Tumor Cells", *Journal of Histochemistry & Cytochemistry 42*(7):961–966, Abstract No. 94284619.

Sugihara, et al. (1991) "Morphology and Modes of Cell Proliferation in Earliest Signet–Ring–Cell Carcinomas Induced in Canine Stomachs by N–Ethyl–N'–Nitro–N–Nitrosoguanidine", *J. Cancer Res. Clin. Oncol. 117*:197–204.

Trosko (1994) "Radiation–Induced Carcinogenesis: Paradigm Considerations", Chapter 14, *Biological Effects of Low Level Exposures: Dose–Response Relationships*:205–241.

Yao, et al. (May 1993) "In situ Hybridization at the Electron Microscopic Level using a Bromodeoxyuridine Labeled DNA Probe", *Biotechnic & Histochemistry 68*(3):169–174, Abstract No. 93333022.

CARCINOGENICITY TESTING SYSTEM

CROSS REFERENCE TO RELATED APPLICATION

This application claims the benefit of U.S. Provisional Application No. 60/026,310, filed on Sep. 18, 1996.

BACKGROUND OF THE INVENTION

There is a consensus that animal, and especially rodent systems, are not ideal for the prediction of the carcinogenicity of various chemicals in humans. Apparently, different species vary in their capacity to repair deoxyribonucleic acid (DNA) after radiation injury, in a manner suggesting correlation with species longevity (Tice, et al. (1985) "DNA Repair and Replication in Aging Organisms and Cells", *The Biology of Aging*, C. E. Finch and E. L. Schneider, Eds., Pages 173–224, Van Nostrand Reinhold Company, New York and Sankar (1994) *Science* 266:1954–1956). Malignancies, too, may be correlated with species longevity (Kim, et al. (1994) *Science* 266:2011–2015). Thus, studies conducted with neoplastic transformation are more readily performed in rodent than in human cells in culture (Borek (1985) *Carcinopenesis* 10:303–316), clearly indicating a higher level of sensitivity to carcinogens in the former than in the latter system(s). Yet a system with human cells in culture to test carcinogenicity would obviously be highly desirable.

SUMMARY OF THE INVENTION

The present invention is directed to an in vitro method for detecting a carcinogenic agent comprising administering a deoxyuridine analog to agglomerated cells, quantitatively measuring said deoxyuridine analog uptake by conventional means and then comparing the results to a control cell sample.

DETAILED DESCRIPTION OF THE INVENTION

The present invention is directed to an in vitro method for detecting the presence of carcinogenic agents. Carcinogenic agents contemplated by the present invention may be "known" or "suspected". Examples of "known" carcinogenic agents include, but are not limited to, asbestos, nitrosamines, polybrominated biphenyls and cigarette smoke condensates. As defined by the present invention, the term "carcinogenic agent" is also meant to include radiation. "Suspected" carcinogens include agents which have been implicated in the promotion of carcinogenesis, but which have not been conclusively proven to cause cancer. Examples of "suspected" carcinogens include, but are not limited to pesticides, herbicides, unsaturated fatty acids, growth factors and hormones.

The present inventor has observed that when cells are exposed to a carcinogen, not only are the exposed cells transformed, the cells proliferate and incorporate the nucleoside analog. On the other hand, normal cells agglomerated into spheroids do not take up the nucleoside analog and maintain their contact inhibition, as defined herein, when brought into proximity with other cells. Based upon these observations, the inventor developed the protocol of the present invention. The determination of whether a particular substance or chemical is a carcinogen is determined by the following method: exposing a cell line, e.g. fibroblast cells to said suspected carcinogen, agglomerating the treated cells; incubating the agglomerated cells with a deoxyuridine analog; labeling the cells which have incorporated the deoxyuridine analog with an antibody to the deoxyuridine analog; and quantitating the amount of cells incorporating the deoxyuridine analog. As a control, the methodology is also performed either without exposing the cells to a carcinogen or by exposing the cells to an agent which is conventionally known not to be a carcinogen. The results from the exposed cells are then compared with the results from the control. The presence of a carcinogen is concluded if the exposed cells incorporate at least two to three times as much nucleoside analog into their DNA as the control.

The cell sample used in accordance with the present invention includes cell lines and biopsied tissue. The cell line used in connection with the present invention is conventional and the skilled artisan can select from numerous cell lines for the instant assay. Examples of cell lines which may be utilized in connection with the present invention include human fibroblast cell lines, IMR-90 (lung), AG 15–22 (foreskin), BALB/C-3T3 and C3H 1OT 1/2 mouse embryonic cells. Cell lines may also be prepared from fibroblasts from human biopsies. It is preferred that the cells are maintained at suitable densities in Eagle's Minimal Essential Medium (MEM) with 15% Fetal Calf Serum (Gibco). Preferably, optimal growth is achieved using low passage cells. In a more preferred embodiment, cell cultures are initiated from inocula of between about $0.4 \times 10^6$ to about $10 \times 10^6$ cells. Most preferably the cells are grown in a monolayer at a density where the cells are not contact inhibited for growth.

Once grown, the cell line is next exposed to the test substance or chemical to determine whether it is a carcinogen. A control cell line is either exposed to a non-carcinogen or the control cell line is not exposed to anything. Obviously, the amount of material exposed to the cell line may also have an effect. The amount of test substance exposed to the cell line is determined by the skilled artisan. In one embodiment of the present invention, the test compound or substance is exposed to the cell line at various concentrations. However, it is preferred that the test substance and potency be selected to approximate conditions to be encountered in vivo (i.e. the carcinogen should not be provided at levels which are toxic). It is to be noted that the control cells, if exposed to a non-carcinogen, are exposed to the non-carcinogen in the same concentration as the cells exposed to the test compound.

The cells (carcinogen-exposed and controls) are next agglomerated to form spheroids. The time interval between carcinogen exposure and agglomeration may be varied, from 0 to to about 7 days, to allow new phenotype expression. As defined by the present invention an "agglomerate" is a tightly packed group of cells formed by the clumping together of formerly dissociated cells. The methodology for preparing spheroids is described in U.S. Pat. No. 5,023,172, which issued Jun. 11, 1994 to Djordjevic, which teachings are incorporated herein by reference. It is preferred that about $5 \times 10^6$ trypsinized cells are dispersed in 10 ml of complete medium (MEM) supplemented with Fetal Calf Serum (FCS), and incubated overnight at 37° C. in a 10 cm petri dish for spheroid formation. After overnight incubation at 37° C., a large number of rounded cell agglomerates form in the petri dish. These spheroid bodies are of various sizes and tend to attach to each other upon manipulation of the petri dish.

It is preferred that spheroids of about 50 to about 70 $\mu$m in diameter be employed in the present methodology. This is obtained by conventional techniques known to the skilled artisan. For example, the desired population of spheroids is obtained by passing the contents of the petri dish through a series of nylon sieves (also termed micrometer filters and obtained from Small Parts Inc., Miami, Fla.) and eluting from the appropriate size sieve with standard medium, e.g. about 20 ml MEM. The selected spheroid suspension, preferably containing about $2\times10^6$ cells is then conventionally counted in a small aliquot, and a desired volume of medium is adjusted to a chosen density of spheroids. In accordance with the present invention, the spheroids formed contain cells which are contact inhibited. By "contact inhibited" or "contact inhibition" is meant cells which do not proliferate as a consequence of their proximity to each other. The phenomenon of contact-inhibition is well known in untransformed cells. (See, e.g. Sakiyama, et al. (1978) *Cancer Research* 38:2854–2858, incorporated herein by reference). Thus, cellular agglomerates of untransformed cells are, by definition, contact-inhibited.

The agglomerated cells are next incubated with a deoxyuridine analog and a thymidilate synthetase inhibitor. By deoxyuridine analog is meant a derivative of a deoxyuridine, which is incorporated by a cell transformed by a carcinogen but not incorporated by untransformed spheroid cells. It is preferred that the deoxyuridine analog is a halogenated deoxyuridine and more specifically, chlorodeoxyuridine, bromodeoxyuridine or iododeoxyuridine and even more preferred the 5-halo isomer thereof. The deoxyuridine analog is preferably present in amounts sufficient to permit uptake thereof by the transformed cell concentrations ranging from about $3\times10^{-6}$ (g/g) to about $1.5\times10^{-5}$ (g/g) relative to the amount of cells present.

The thymidilate synthetase inhibitor is an inhibitor of the enzyme. Without wishing to be bound, it is believed that thymidilate synthetase interferes with the assay in that it acts to facilitate de novo synthesis of thymidine, thus diluting the added deoxyuridine analog. Therefore, by adding an inhibitor to the assay, the activity of thymidilate synthetase is significantly curtailed thereby minimizing its interference with the assay. The preferred inhibitor is fluorouridine, especially 5-fluorouridine. However, the present invention contemplates other thymidilate synthetase inhibitors, as conventionally known in the art.

The thymidilate synthetase inhibitor is present in effective amounts to inhibit the thymidilate synthetase. The thymidilate synthetase inhibitor is preferably present in amounts ranging from about $10^{-9}$ (g/g) to about $10^{-7}$ (g/g).

In a preferred embodiment, the agglomerated cells are incubated with 5-bromodeoxyuridine (BUdR) or 5-iododeoxyuridine (IUdR) in combination with a thymidilate synthetase inhibitor. In a most preferred embodiment, the agglomerated cells are incubated with 5-bromodeoxyuridine and 5-fluorodeoxyuridine (FUdR) (which is known to inhibit thymidilate synthetase and facilitate BUdR incorporation) at a concentration of about $10^{-6}$ M BUdR to about $10^{-4}$ M BUdR, preferably from $10^{-5}$ M BUdR to $5\times10^{-5}$ M BUdR, and more preferably $2\times10^{-5}$ M BUdR and from about $2\times10^{-9}$ M to about $2\times10^{-7}$ M FUdR, preferably $2\times10^{-8}$ M FUdR in 10 cm petri dishes for a sufficient time to exceed one full cell cycle. The timing of one full cell cycle may conventionally be determined separately in non-contact inhibited cells.

In connection with the present invention, it has been determined that non-contact inhibited (e.g. proliferating cells) will incorporate the deoxyuridine analog, e.g. BUdR into their DNA. "Normal" cells (e.g. untransformed cells) are contact-inhibited and are generally understood not to progress through the cell cycle when surrounded by other cells. Therefore normal cells do not incorporate the deoxyuridine analog, e.g. BUdR.

In connection with the present invention, the inventor has observed that an important step in the transformation of normal cells to neoplastic cells is the loss of contact-inhibition of cell cycle progression and thus an increased proliferative capacity.

It has now been observed by the present inventor that exposing cells to known or suspected carcinogens will result in a loss of contact-inhibition which is indicative of carcinogen-induced transformation.

It has also been observed by the present inventor that detection of transformed cells is accomplished by measuring incorporation therein of the deoxyuridine analog. It has further been observed that the incorporation of a deoxyuridine analog, such as BUdR will increase as a consequence of prior treatment with a carcinogen in cells under conditions where DNA synthesis does not normally occur (e.g. in contact-inhibited spheroids). Moreover, the inventor has observed that untransformed cells (e.g. human fibroblast controls) in culture do not incorporate the deoxyuridine analog, e.g. BUdR when agglomerated in the form of spheroids. However, when untransformed cells are dispersed (e.g. allowed to spread on the growth surface of a culture vessel before administration of the deoxyuridine analog), the deoxyuridine analog, such as BUdR is incorporated and the cells become sensitized to visible light.

Following incubation, the agglomerates are conventionally tested by techniques known in the art to detect the deoxyuridine analog, e.g. flow cytometry. Flow cytometry measures the forward light scattering of discrete particles as they individually pass a laser beam and various light detectors. The magnitude of this light scattering measures the size of the particle, permitting selection (gating) of particles having the dimensions of cells. Use of a commercially available fluorescent antibody to the deoxyuridine analog containing DNA permits the fluorescence of this antibody (fluorescein) to be used to select (gate) those cells which have incorporated the deoxyuridine analog into their DNA (and hence from the experimental design, cells which were in DNA synthesis at the time of exposure to the deoxyuridine analog). The flow cytometer is a Coulter EPICS V Model 752 with dual argon lasers, using a 76 $\mu$m diameter orifice flow cell. The excitation wavelength is 488 nm and emission is measured at >610 nm. The cross sectional area of the laser beam is $16\times160$ $\mu$m, which covers the entire cell as it passes through the beam.

Finally, statistical evaluations of carcinogenic activity are performed to quantitate the transforming ability of known or suspected carcinogens. The presence of a carcinogen is concluded if the exposed cells incorporate at least two times as much nucleoside analog into their DNA as the control cells.

We claim:

1. An in vitro method for determining whether a test compound is a carcinogen comprising:
    (a) exposing a cell sample to said test compound for a period of time up to about seven days;
    (b) agglomerating said cell sample to produce an aglomerated cell sample;
    (c) administrating a deoxyuridine analog and a thymidilate synthetase inhibitor to said agglomerated cell sample, wherein said deoxyuridine analog is a halogenated deoxyuridine which is incorporated by cells transformed by a carcinogen and is not incorporated byuntransformed spheroid cells;

(d) dispersing said agglomerated cell sample on a growth surface of a culture vessel;

(e) labeling said cell sample with an antibody which specifically binds to said deoxyuridine analog;

(f) detecting and quantitating the amount of said deoxyuridine analog incorporated by said cell sample;

(g) repeating steps (b) through (f) with a control cell sample without exposing said control cell sample to said test compound, thereby detecting and quantitating the amount of said deoxyuridine analog incorporated by said control cell sample;

(h) comparing the amount of said deoxyuridine analog incorporated by said cell sample of step (a) to the amount of said deoxyuridine analog incorporated by said control cell sample of step (g); and (i) determining whether the amount of said deoxyuridine analog incorporated by said cell sample of step (a) is at least greater than about two times the amount of said deoxyuridine analog incorporated by said control cell sample of step (g), to conclude that said test compound is a carcinogen.

* * * * *